US007495050B2

(12) United States Patent
Lai et al.

(10) Patent No.: US 7,495,050 B2
(45) Date of Patent: *Feb. 24, 2009

(54) ASSOCIATIVE THICKENERS FOR AQUEOUS SYSTEMS

(75) Inventors: John Ta-Yuan Lai, Broadview Heights, OH (US); Shui-Jen Raymond Hsu, Westlake, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 554 days.

This patent is subject to a terminal disclaimer.

(21) Appl. No.: 10/923,271

(22) Filed: Aug. 20, 2004

(65) Prior Publication Data

US 2005/0038280 A1 Feb. 17, 2005

Related U.S. Application Data

(63) Continuation-in-part of application No. 10/681,679, filed on Oct. 8, 2003, now Pat. No. 7,335,788, which is a continuation-in-part of application No. 10/278,335, filed on Oct. 23, 2002, now Pat. No. 7,205,368, which is a continuation-in-part of application No. 09/505,749, filed on Feb. 16, 2000, now Pat. No. 6,596,899.

(51) Int. Cl.
*C08K 5/36* (2006.01)
*C08K 5/00* (2006.01)
*C07C 329/00* (2006.01)
*C07C 327/00* (2006.01)

(52) U.S. Cl. .................. 524/280; 524/392; 558/243; 558/244; 558/245; 560/302

(58) Field of Classification Search ............. 558/243, 558/244, 245; 560/302; 524/280, 392
See application file for complete search history.

(56) References Cited

U.S. PATENT DOCUMENTS

| 3,285,945 A | 11/1966 | Wember |
| 3,285,949 A | 11/1966 | Siebert |
| 3,770,698 A | 11/1973 | Riew |
| 3,860,641 A | 1/1975 | Zengel et al. |
| 3,928,491 A | 12/1975 | Waters |
| 3,992,432 A | 11/1976 | Napier et al. |
| 4,079,028 A | 3/1978 | Emmons et al. |
| 4,180,491 A | 12/1979 | Kim et al. |
| 4,425,485 A | 1/1984 | Sone et al. |
| 4,514,552 A | 4/1985 | Shay et al. |
| 4,533,467 A * | 8/1985 | Kimble et al. ............... 209/167 |
| 4,552,929 A | 11/1985 | Devaux et al. |
| 4,722,962 A | 2/1988 | Shay et al. |
| 4,769,419 A | 9/1988 | Dawdy |
| 5,055,515 A | 10/1991 | Backderf |
| 5,140,068 A | 8/1992 | Siebert et al. |
| 5,157,077 A | 10/1992 | Siebert et al. |
| 5,198,510 A | 3/1993 | Siebert et al. |
| 5,258,445 A | 11/1993 | Sperk, Jr. et al. |
| 5,280,068 A | 1/1994 | Siebert et al. |
| 5,312,956 A | 5/1994 | Bertsch |
| 5,385,963 A | 1/1995 | McBain et al. |
| 5,807,748 A | 9/1998 | Bailey |
| 6,153,705 A | 11/2000 | Corpart et al. |
| 6,380,335 B1 | 4/2002 | Charmot et al. |
| 6,395,850 B1 | 5/2002 | Charmot et al. |
| 6,545,098 B1 | 4/2003 | Bouhadir et al. |
| 2004/0073056 A1 | 4/2004 | Lai |

FOREIGN PATENT DOCUMENTS

| EP | 0704460 | 4/1996 |
| GB | 1223524 | 2/1971 |
| WO | 98/01478 | 1/1998 |
| WO | 99/05099 | 2/1999 |
| WO | 99/31144 | 6/1999 |
| WO | 99/35177 | 7/1999 |

OTHER PUBLICATIONS

World Polymer Congress, 37th International Symposium on Macromolecules, Jul. 12-17, 1998, Gold Coast, Australia.
John Chiefari, et al., "Living Free-Radical Polymerization by Reversible Addition-Fragmentation Chain Transfer: The RAFT Process", *CSIRO Molecular Science, Bag 10*, Clayton South. Clayton, Victoria 3169, Australia, Revised Manuscript.
H.C. Godt, Jr., and R.E. Wann, *Journal of Organic Chemistry*, vol. 26, "The Synthesis of Organic Trithiocarbonates[1]", pp. 4047-4050, Oct. 1961.
Iacopo Degani, et al, *Synthesis*, "Phase-Transfer Synthesis of Symmetrical and Unsymmetrical Dialkyl Trithiocarbonates", pp. 894-899, Nov. 1986.
Julia Kristina, et al., CSIRO, Division of Chemicals and Polymers, *Macromol, Symp.* 111, "A New Form of Controlled Growth Free Radical Polymerization", pp. 13-23, 1996.
Albert W.M. Lee, et al, *Synthetic Comm.*, "One Pot Phase Transfer Synthesis of Trithiocarbonates from Carbon Disulphide and Alkyl Halides", vol. 18, No. 13, pp. 1531-1536, 1988.
Man-kit Leung, et al, *Journal of Chemical Research (S)*, "A Novel One-step Synthesis of Symmetrical Dialkyl Trithiocarbonates", pp. 478-479, 1995.

(Continued)

Primary Examiner—Taylor Victor Oh
(74) Attorney, Agent, or Firm—Thoburn T. Dunlap; Hudak, Shunk & Farine Co., L.P.A.

(57) ABSTRACT

Thiocarbonate compounds which, in one embodiment, are utilized as a rheology modifier or associative thickener. The thiocarbonate compounds thicken or increase the viscosity of a composition, preferably an aqueous composition when used in an effective amount. In one preferred embodiment, the thiocarbonate compounds include at least one hydrophilic group containing repeat unit such as derived from acrylic acid, and at least one hydrophobic group to enhance association with other compounds and thus increase viscosity of a composition. Aqueous composition comprising a latex and thiocarbonate associative thickeners are described.

9 Claims, No Drawings

OTHER PUBLICATIONS

Daniel Taton, et al, *Macromol,ecular Rapid Communication*, "Direct Synthesis of Double Hydrophilic Statistical Di- and Triblock Copolymers Comprised of Acrylamide and Acrylic Acid Units via the MADIX Process", vol. 22, No. 18, pp. 1497-1503, 2001.

M. Destarac, et al, *Macromolecular Rapid Communication*, "Dithiocarbamates as Universal Reversible Addition-Fragmentation Chain Transfer Agents", vol. 21, No. 15, pp. 1035-1039, 2000.

Roshan T.A. Mayadunne, et al., *Macromolecules*, "Living Radical Polymerization with Reversible Addition—Fragmentation Chain Transfer (RAFT Polymerization) Using Ditriocarbamates as Chain Transfer Agents", vol. 32, pp. 6977-6980, 1999.

Yusuf Yagci et al., *Progress Polymer Science*, "Light-Induced Synthesis Of Block And Graft Copolymers", vol. 15, pp. 551-601, 1990.

*Polymer Handbook, Third Edition*, J. Brandrup et al., John Wiley & Sons:New York, "6. Peresters and Peroxy Carbonates", pp. 11/53, 1989.

"The Chemistry of Free Radical Polymerization", Moad and Solomon, Pergamon, London, pp. 53-95, 1995.

Eric J. Goethe, CRC Press, Boca Raton, Florida, *Telechelic Polymers: Synthesis and Applications*, Chapter 4—Telechelics By Free Radical Polymerization Reactions, pp. 61-94 and Chapter 10—Terminal Transformation Of Telechelics, pp. 229-259, 1989.

"New Associative Thickeners and Their Use in Waterborne and High-Solids Coatings", Johan Bieleman, CONDEA Servo BV, Coating Additives Division, Delden, The Netherlands, Nov. 1999, pp. 46-56.

"A New Class of Alkali-Swellable Associative Thickeners", G. Shay, Union Carbide Chemicals & Plastics, *Surface Coatings International*, vol. 76, pp. 446-462, 1993.

A. Bistrzycki et al., "Synthesis of Derivatives of 1,3-Ox[a]thiophane", *Helvetica Chimica Acta*, vol. 3, 1920, pp. 447-467.

C.W. Pluijgers et al., "Plant Growth-Regulating Activity of S-Carboxymethyl-N,N-Dimethyldithiocarbamate and Related Compounds", *Recueil Des Travaux Chmiiques Des Pays-Bas*, vol. 80, No. 9/10, Sep. 9, 1961, pp. 1089-1100.

L. Field, et al., "Preparation and Chlorinolysis Of α-Mercaptodiethylacetic Acid", *Journal of the American Chemical Society*, vol. 74, No. 18, Sep. 20, 1952, pp. 4707-4708.

F. Andreani, et al., "New α-Substituted Arylthioacetic Derivatives Forming Analogues of Clofibrate", *IL Farmaco, Edizione Scientifica*, vol. 30, No. 10, Oct. 1975, pp. 847-858.

Iacopo Degani, et al., "Phase-Transfer Synthesis of Symmetrical and Unsymmetrical Dialkyl Trithiocarbonates", *Synthesis*, pp. 894-899, Nov. 1986.

"A New Form of Controlled Growth Free Radical Polymerization", Julia Kristina, et al., CSIRO, Division of Chemicals and Polymers, *Macromol. Symp.* III, pp. 13-23 (1996).

Albert W.M. Lee, et al., "One Pot Phase Transfer Synthesis of Trithiocarbonates from Carbon Disulphide and Alkyl Halides", *Synthetic Comm.*, vol. 18, No. 13, pp. 1531-1536, 1988.

Yusuf Yagci et al., *Progress in Polymer Science*, vol. 15, "Light-Induced Synthesis Of Block And Graft Copolymers", pp. 551-601, 1990.

*Polymer Handbook, Third Edition*, J. Brandup et al., John Wiley & Sons: New York, "6. Peresters and Peroxy Carbonates", p. 11/53, 1989.

Moad and Solomon, Pergamon, London, "The Chemistry of Free Radical Polymerization", pp. 53-95, 1995.

Eric J. Goethals, CRC Press, Boca Raton, Florida, *Telechelic Polymers: Synthesis and Applications*, Chapter 4—Telechelics By Free Radical Polymerization Reactions, pp. 61-94, and Chapter 10—Terminal Transformation of Telechelics, pp. 229-259, 1989.

"A New Class of Alkali-Swellable Associative Thickeners", G. Shay, Union Carbide Chemicals & Plastics, 410 Gregson Drive, Cary, North Carolina 27511, USA, Surface Coatings International, vol. 76, pp. 446-462.

R.J. Stoodley, "Studies Related to Penicillins. Part II. The Rearrangement of 6-β-Aminopencillanic Acid to 2,3-Dihydro-6-Methoxycarbonyl-2,2-Dimethyl-1,4-Thiazin-3-One", Journal of the Chemical Society, Section C: Organic Chemistry, No. 23, 1968, pp. 2891-2894.

United States Patent and Trademark Office Action mailed on Jun. 25, 2007 for U.S. Appl. No. 11/206,393.

United States Patent and Trademark Office Action mailed on Nov. 1, 2007 for U.S. Appl. No. 11/206,393.

\* cited by examiner

ASSOCIATIVE THICKENERS FOR AQUEOUS SYSTEMS

CROSS REFERENCE

This patent application is a continuation-in-part application based on U.S. application Ser. No. 10/681,679 filed Oct. 8, 2003, now U.S. Pat. No. 7,335,788 for S-($\alpha,\alpha'$-Disubstituted-$\alpha''$-Acetic Acid) Substituted Dithiocarbonate Derivatives for Controlled Radical Polymerizations, Process and Polymers Made Therefrom, which is a continuation-in-part application based on U.S. application Ser. No. 10/278,335, filed Oct. 23, 2002 now U.S. Pat. No. 7,205,368 for S-($\alpha,\alpha'$-Disubstituted-$\alpha''$-Acetic Acid) Substituted Dithiocarbonate Derivatives for Controlled Radical Polymerizations, Process and Polymers Made Therefrom which in turn is a continuation-in-part based on U.S. application Ser. No. 09/505,749 filed Feb. 16, 2000, now U.S. Pat. No. 6,596,899 issued Jul. 22, 2003, for S,S'-Bis-($\alpha,\alpha'$-Disubstituted-$\alpha''$-Acetic Acid)—Trithiocarbonates And Derivatives As Initiator—Chain Transfer Agent—Terminator For Controlled Radical Polymerizations And The Process For Making The Same.

FIELD OF THE INVENTION

The present invention relates to thiocarbonate compounds which, in one embodiment, are utilized as a rheology modifier or associative thickener. The thiocarbonate compounds thicken or increase the viscosity of a composition, preferably an aqueous based composition when used in an effective amount. In one preferred embodiment, the thiocarbonate compounds include at least one hydrophilic group containing repeat unit preferably derived from (meth)acrylic acid or (meth)acrylamide or the like, and at least one hydrophobic group to enhance association with other compounds and thus increase viscosity, especially high shear viscosity, of a composition. Aqueous systems comprising a latex and the associative thickeners are also disclosed.

BACKGROUND OF THE INVENTION

Among thickeners, some of the most significant thickeners are water soluble polymers containing hydrophobic groups which are capable of forming intermolecular associations and adsorbing onto the surface of dispersed particles. This class of polymers is referred to as associative thickeners.

Associative thickeners or rheology modifiers provide necessary processing and performance characteristics to various compositions having diverse end uses. For example, thickeners are used in aqueous latex paints to provide a desired viscosity and to stabilize emulsions and pigment dispersions. Associative thickeners are used in waterborne coatings to improve the flow and leveling of coating films, improve film build and film formation, improve gloss, and reduce roller spatter. Thickeners are also used in the preparation of cosmetics and pigment pastes; textile manufacturing; and in many processes that involve the treatment of water including oil drilling and enhanced oil recovery operations.

Aqueous systems utilizing associative thickeners are often required to display an acceptable response to shear induced deformation encountered in the manufacture of the system, and also during application or use.

Associative thickeners are either naturally or synthetically derived compounds. Modified natural compounds which have been utilized in the art for many years include starch, cellulose, alginate, and protein. The natural thickeners generally include building blocks of polysaccharide units or amino acids, and grafting of selected moieties onto the backbone provides for modified versions utilized in different applications. The synthesized polymeric associative thickeners include acrylic-based polymers derived from acrylic acid or acrylate esters among others. The addition of hydrophobic moieties to the acrylic-based polymers has also been performed. Further synthetic associative thickeners include hydrophobically modified polyether-based polyurethanes and hydrophobically modified ethoxylated urethane resins which generally consists of polyethylene glycol units of varying length connected by urethane linkages with the polymer terminated with hydrophobic end groups. The prior art acrylic acid or acrylate associative thickeners typically exhibit inferior properties when compared to polyurethane associative thickeners, even at very high concentration.

U.S. Pat. Nos. 4,079,028, 4,180,491, and 4,425,485 disclosed the use of polyurethane having hydrophobic branching groups as thickeners. U.S. Pat. No. 4,514,552 discloses the use of ethoxylated hydrophobes in acrylic emulsions to make alkali soluble thickeners.

SUMMARY OF THE INVENTION

The associative thickeners of the present invention are derived from a thiocarbonate group containing compound and comprise both hydrophilic and hydrophobic groups within the same compound. The thiocarbonate associative thickeners are utilized in aqueous systems preferably also comprising a latex to increase the viscosity of the system. In preferred embodiments, the thiocarbonate thickeners are random or block copolymers. The hydrophobic group can be located at the terminal end of the (co)polymer, or pendant from the backbone, or a combination thereof.

Various methods are employed to prepare the thiocarbonate associative thickeners of the present invention. In one embodiment, a thiocarbonate associative thickener is prepared by esterification of the thiocarbonate, which incorporates terminal hydrophobic groups, followed by polymerization to incorporate various hydrophilic group containing monomers such as acrylic acids or acrylates into the backbone of the thiocarbonate compound. In a further embodiment, hydrophilic and hydrophobic groups are added to a thiocarbonate compound through polymerization of monomers containing such groups into the backbone of the thiocarbonate compound. In yet another embodiment, terminal hydrophobic groups are added through esterification of said groups present on the thiocarbonate compounds after a polymerization step which incorporates at least a hydrophobic group containing monomer into the thiocarbonate.

DETAILED DESCRIPTION OF THE INVENTION

Thiocarbonate Compounds

The thiocarbonate compounds utilized in the present invention are preferably polythiocarbonates such as dithiocarbonate or trithiocarbonate compounds and derivatives thereof. By the term "thiocarbonate", it is meant a compound having at least one segment having the formula:

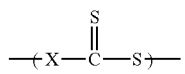

wherein X comprises OR, SR, or $NR_2$ for example with R being various hydrocarbon, heteroatom and/or hydrogen containing structures or the like preferably as illustrated hereinbelow, but not limited thereto.

Suitable trithiocarbonate compounds for use in the present invention, but not limited thereto, are disclosed in U.S. Pat. No. 6,596,899 to Lai, herein fully incorporated by reference. In one embodiment, trithiocarbonate compounds have the following general formula:

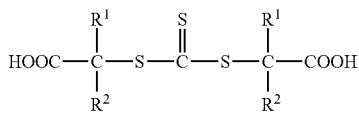

wherein $R^1$ and $R^2$, independently, is the same or different, and is a linear or branched alkyl having from 1 to about 6 carbon atoms, or a $C_1$ to about $C_6$ alkyl having one or more substituents, or one or more aryls or a substituted aryl group having 1 to 6 substituents on the aryl ring, where the one or more substituents, independently, comprise an alkyl having from 1 to 6 carbon atoms; or an aryl; or a halogen such as fluorine or chlorine; or a cyano group; or an ether having a total of from 2 to about 20 carbon atoms such as methoxy, or hexanoxy; or a nitro; or combinations thereof. Examples of such compounds include s,s'-bis-2-methyl-2-propanoic acid-trithiocarbonate and s,s'-bis-(2-phenyl-2-propanoic acid)-trithiocarbonate. $R^1$ and $R^2$ can also form or be a part of a cyclic ring having from 5 to about 12 total carbon atoms. $R^1$ and $R^2$ are preferably, independently, methyl or phenyl groups.

The abbreviated reaction formula for one method for the preparation of s,s'-bis-(α,α'-disubstituted-α"-acetic acid)-trithiocarbonates is generally written as follows:

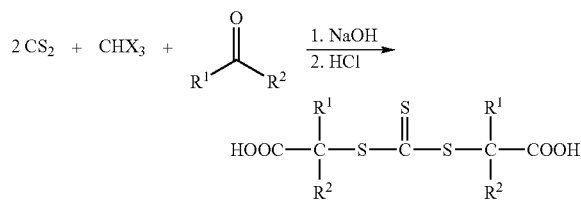

The process utilized to form s,s'-bis-(α,α'-disubstituted-α"-acetic acid)-trithiocarbonate compounds is generally a multi-step process and includes combining the carbon disulfide and a base whereby an intermediate trithio structure is formed. Ketone can serve as solvent for the carbon disulfide/base reaction and thus can be added in the first step of the reaction. In the second step of the reaction, the haloform, or haloform and ketone, or a α-trihalomethyl-α-alkanol are added to the trithio intermediate mixture and reacted in the presence of additional base. The formed reaction product, is subsequently acidified, thus completing the reaction and forming the above described s,s'-bis-(α,α'-disubstituted-α"-acetic acid)-trithiocarbonate compound.

Another aspect of present invention utilizes trithiocarbonate compounds having the following formula:

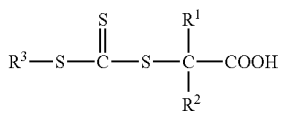

wherein $R^3$ comprises a benzyl group, $C_1$-$C_{18}$ alkyl, or substituted alkyl such as halogen, hydroxyl, or alkoxy, $C_1$-$C_{18}$ hydroxyalkyl, aralkyl, hydroxyalkyl, cyanoalkyl, aminoalkyl, carboxylalkyl, carboalkoxyalkyl or mercaptoalkyl, and $R^1$ and $R^2$ are defined hereinabove. The resulting compound is an s-substituted-s'-(α,α'-disubstituted-α"-acetic acid)-trithiocarbonate.

Dithiocarbonate compounds which are utilized in some embodiments of the present invention are disclosed in U.S. application Ser. No. 10/278,335 filed Oct. 23, 2002 and U.S. application Ser. No. 10/681,679 filed Oct. 8, 2003, herein fully incorporated by reference. In one embodiment the dithiocarbamate compounds have the following formula:

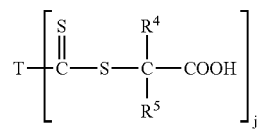

wherein j is 1 or 2, with the proviso that when j is 1, T is —(NR$^6$, R$^7$); and when j is 2, T is a divalent radical having a nitrogen atom directly connected to each carbon atom of the two thiocarbonyl groups present;

wherein $R^4$ and $R^5$, independently, is the same or different, is optionally substituted, and is a linear or branched alkyl having from 1 to about 6 or about 12 carbon atoms; or an aryl group having from 6 to about 18 carbon atoms, optionally containing heteroatoms;

wherein the $R^4$ and/or $R^5$ substituents, independently, comprise an alkyl having from 1 to 6 carbon atoms; an aryl group; a halogen; a cyano group; an ether having a total of from 2 to about 20 carbon atoms; a nitro; or combinations thereof. $R^4$ and $R^5$ can also form or be a part of a substituted or unsubstituted cyclic ring having from 3 to about 12 total carbon atoms wherein the substituents are described above. $R^4$ and $R^5$ are preferably, independently, methyl or phenyl groups;

wherein $R^6$ and $R^7$, independently, is the same or different, optionally is substituted, optionally contains heteroatoms; and is hydrogen; a linear or branched alkyl having from 1 to about 18 carbon atoms, an aryl group having from about 6 to about 18 carbon atoms optionally saturated or unsaturated; an arylalkyl having from about 7 to about 18 carbon atoms; an alkenealkyl having from 3 to about 18 carbon atoms; or derived from a polyalkylene glycol ether having from 3 to about 200 carbon atoms. $R^6$ and $R^7$ can also be derived from amines such as, but not limited to, piperazine, morpholine, pyrrolidine, piperidine, 4-alkylamino-2,2,6,6-tetramethyl piperidine, 1-alkylamioalkyl-3,3,5,5-tetramethyl-2 piperazinone, hexamethyleneimine, phenothiazine, iminodibenzyl, phenoxazine, N,N'-diphenyl-1,4-phenylenediamine, dicyclohexylamine and derivatives thereof. $R^6$ and $R^7$ can also form a substituted or unsubstituted cyclic ring, optionally containing heteroatoms, along with the nitrogen having a total of from 4 to about 12 carbon atoms, such as benzotriazole, tolyltriazole, imidazole, 2-oxazolidone, 4,4-dimethyloxazolidone and the like. The $R^6$ and $R^7$ substituents, independently, can be the same as described herein with respect to $R^{13}$. $R^6$ and $R^7$ are preferably, independently, a phenyl group or an alkyl or substituted alkyl having from 1 to about 18 carbon atoms such as a methyl group, or $R^6$ and $R^7$, independently, are hexamethylene.

When j is 1, T of above formula is —(NR⁶R⁷) and the dithiocarbamate compound is a S-(α,α'-disubstituted-α"-acetic acid) dithiocarbamate generally having the following formula:

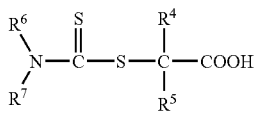

wherein $R^4$, $R^5$, $R^6$, and $R^7$ are as defined hereinabove.

When j is 2, the dithiocarbarbamate compound is a bis-S-(α,α'-disubstituted-α"-acetic acid) dithiocarbamate having the following formula:

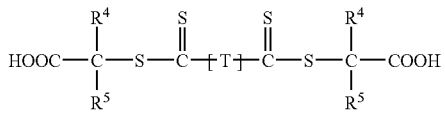

wherein $R^4$ and $R^5$ are defined hereinabove; and wherein T is a divalent bridging radical having a nitrogen atom directly connected to each of the thiocarbonyl groups present.

In one embodiment T is:

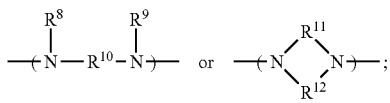

wherein $R^8$ and $R^9$, independently, is the same or different, is optionally substituted, and is hydrogen, a linear or branched alkyl having from 1 to about 18 carbon atoms, an aryl group having from about 6 to about 18 carbon atoms, an arylalkyl having from 7 to about 18 carbon atoms, or an alkenealkyl having from 3 to about 18 carbon atoms, wherein the substitutents can be the same as described herein for $R^1$ and $R^2$;

wherein $R^{10}$ is optionally substituted, and is non-existent, or an alkylene group having from 1 to about 18 carbon atoms with about 1 to about 6 carbon atoms preferred, or derived from a polyalkylene glycol ether having from 3 to about 200 carbon atoms, wherein the substituents can be the same as described herein for $R^1$ and $R^2$ or are heteroatoms such as oxygen, nitrogen, sulfur or phosphorous; and wherein $R^{11}$ and $R^{12}$ independently, is the same or different, and is optionally substituted as described for $R^1$ and $R^2$, and is an alkylene group having from 1 to about 4 carbon atoms, with $R^{11}$ and $R^{12}$ preferably having a collective total of 3 to 5 carbon atoms.

In further embodiments, T is:

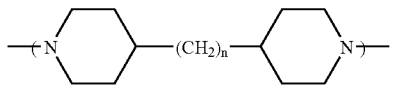

wherein n is 0 to about 18, with 0 to about 6 preferred;

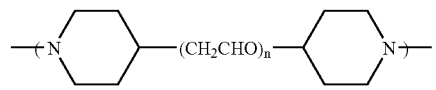

wherein n is 0 to about 18, with 0 to about 6 preferred;

Some specific non-limiting examples of T bridging radicals are:

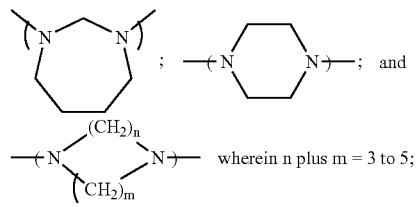

wherein n plus m = 3 to 5;

The S-(α,α'-disubstituted-α"-acetic acid) or bis-S-(α,α'-disubstituted-α"-acetic acid) dithiocarbamates are generally a reaction product of a metal salt of a dithiocarbamate, a haloform, and a ketone. A phase transfer catalyst, solvent, and a base such as sodium hydroxide or potassium hydroxide can also be utilized to form the S-(α,α'-disubstituted-α"-acetic acid) or bis S-(α,α'-disubstituted-α"-acetic acid) dithiocarbamates.

It is to be understood throughout the application formulas, reaction schemes, mechanisms, etc., and the specification that metals such as sodium or bases such as sodium hydroxide are referred to and the application of the present invention is not meant to be solely limited thereto. Other metals or bases such as, but not limited to, potassium and potassium hydroxide, respectively, or combinations thereof are contemplated by the disclosure of the present invention.

Alkoxy dithiocarbonate compounds are utilized in some embodiments of the present invention and having the following general formula:

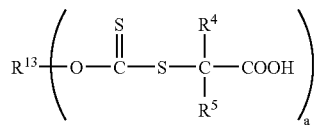

wherein $R^4$ and $R^5$ are as defined hereinabove;

wherein $R^{13}$ is optionally substituted, and can be a linear or branched alkyl having from 1 to about 12 carbon atoms; an aryl group, optionally saturated or unsaturated; an arylalkyl having from 7 to about 18 carbon atoms; an acyl group; an alkenealkyl having from 3 to about 18 carbon atoms; an alkene group; an alkylene group; an alkoxyalkyl; derived from a polyalkylene glycol; derived from a polyalkylene glycol monoalkyl ether having from 3 to 200 carbon atoms; derived from a polyalkylene glycol monoaryl ether having from 3 to 200 carbon atoms; a polyfluoroalkyl such as 2-trifluoroethyl; a phosphorous containing alkyl; or a substituted or unsubstituted aryl ring containing heteroatoms. Alkyl and alkylene groups from 1 to 6 carbon atoms are preferred;

wherein the $R^{13}$ substituents comprise an alkyl having from 1 to 6 carbon atoms; an aryl; a halogen such as fluorine or chlorine; a cyano group; an amino group; an alkene group; an alkoxycarbonyl group; an aryloxycarbonyl group; a carboxy group; an acyloxy group; a carbamoyl group; an alkylcarbonyl group; an alkylarylcarbonyl group; an arylcarbonyl group; an arylalkylcarbonyl group; a phthalimido group; a maleimido group; a succinimido group; amidino group; guanidimo group; allyl group; epoxy group; alkoxy group; an alkali metal salt; a cationic substitutent such as a quaternary ammonium salt; a hydroxyl group; an ether having a total of from 2 to about 20 carbon atoms such as methoxy, or hexanoxy; a nitro; sulfur; phosphorous; a carboalkoxy group; a heterocyclic group containing one or more sulfur, oxygen or nitrogen atoms, or combinations thereof; and wherein "a" is 1 to about 4, with 1 or 2 preferred.

The compounds of the above formula are generally identified as O-alkyl-S-(α,α'-disubstituted-α"-acetic acid) xanthates. The O-alkyl-S-(α,α'-disubstituted-α"-acetic acid) xanthates are generated as the reaction product of an alkoxylate salt, carbon disulfide, a haloform, and a ketone. Alternatively, a metal salt of xanthate can be utilized in place of the alkoxylate salt and carbon disulfide.

The general reaction mechanism for forming the O-alkyl-S-(α,α'-disubstituted-α"-acetic acid) xanthates is as follows:

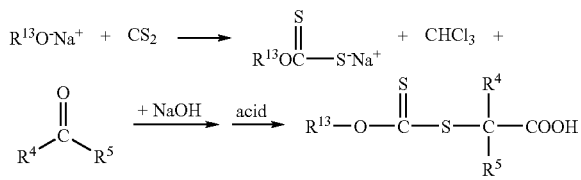

wherein $R^4$, $R^5$, and $R^{13}$ are defined herein.

Hydrophobic Groups

The thiocarbonate associative thickeners include a hydrophobic group or segment. It is believed that the hydrophobic groups associate with each other intermolecularly, or with other polymer or emulsion particles present in an aqueous system and increase the viscosity thereof. It has been found that the thiocarbonate associative thickeners of the invention exhibit desirable viscosity at both low and high shear. The thiocarbonate associative thickener compounds include at least one, and preferably two or more hydrophobic group(s) per molecule. The hydrophobic groups are incorporated into the thiocarbonate compound by reacting the thiocarbonate compound with a monomer, alcohol, or other compound containing the hydrophobe group. For example, carboxyl-terminated thiocarbonates can be esterified with an alcohol comprising a hydrophobic portion. Upon reaction, each hydrophobe group becomes a pendant or terminal group on the thiocarbonate associative thickener. The molecular weight and distribution can be regulated during polymerization so that the low shear viscosity and the polymer architecture can be controlled.

In one embodiment, the hydrophobic group includes a long chain alkyl group having generally from about 3 to about 50 carbon atoms, desirably from about 6 to about 30 carbon atoms, and preferably from about 12 to about 22 carbon atoms. A group of (ether)alcohol compounds having a hydrophobic group has one of the following formulae:

$$R^{14}\text{-}[O\text{-}(CH_2)_y]_n\text{-}OH \text{ or}$$

$$R^{14}\text{-}[O\text{-}(CHR^{15})_y]_n\text{-}OH$$

wherein $R^{14}$ is an alkyl group having generally from about 3 to about 50 carbon atoms, desirably from about 6 to about 30 carbon atoms, and preferably from about 12 to about 22 carbon atoms; wherein each $R^{15}$, independently, is hydrogen, or an alkyl group of from 1 to about 2 carbon atoms; wherein y is generally from 1 to about 12 and preferably 2 to about 6; and each n is the same or different, and is generally 0 or 1 to about 200, and preferably from 0 or 1 to about 50. For example, when y is 2 and both $R^{15}$'s are hydrogen, the hydrophobic group is derived from a polyethylene glycol monoether. Likewise, when y is 2, one $R^{15}$ is hydrogen and the second is —$CH_3$, the hydrophobic group is derived from a polypropylene glycol monoether. When y is 2, $R^{15}$ is hydrogen or —$CH_3$, and n is greater than 1, the hydrophobic group contains a random or block copolymer of poly(ethylene/propylene)glycol monoether. The hydrophobic group contains a poly-1,3-propylene glycol monoether when y is 3 and $R^{15}$ is hydrogen.

In a further embodiment, the hydrophobic group is a part of an unsaturated monomer, such as an acrylate monomer, polymerizable with the thiocarbonate compound. Unsaturated acrylate monomers containing a hydrophobic functional group in one embodiment have the general formulae:

$$CH_2=CH\text{-}COO\text{-}[(CH_2)_y\text{-}O]_n\text{-}R^{14} \text{ or}$$

$$CH_2=(CR^{16})COO\text{-}[(CHR^{15})_y\text{-}O]_n\text{-}R^{14}$$

wherein $R^{14}$, $R^{15}$, y, and n are defined hereinabove, and wherein $R^{16}$ is hydrogen or a methyl group.

A terminal hydrophobic group is added to the thiocarbonate compound via an esterification reaction of the acid end group(s) thereon. Some non-limiting examples of reaction mechanisms are as follows:

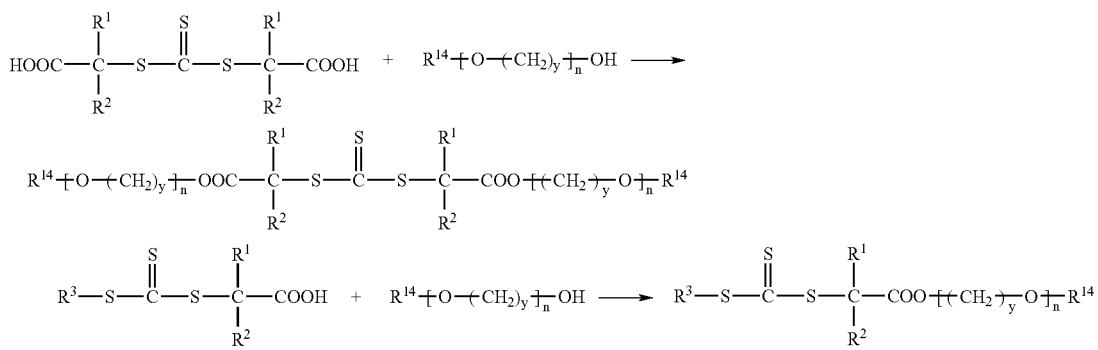

-continued

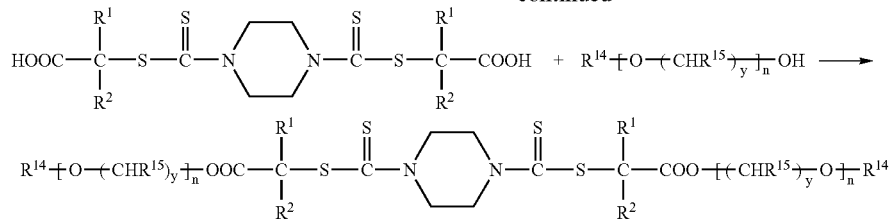

wherein $R^1$, $R^2$, $R^3$, $R^{14}$, $R^{15}$, y, and n are defined herein.

The esterification reaction is performed by combining the thiocarbonate compound and the hydrophobe group containing compound in a suitable reaction vessel. In one embodiment, an effective amount of an acid catalyst is utilized such as, but not limited to, p-toluene sulfonic acid, methane sulfonic acid, hypophosphoric acid, sulfuric acid, with p-toluene sulfonic acid being preferred.

The reactants are heated to a temperature generally from about 35° C. to about 150° C., preferably about 75° C. to about 125° C. for a period of time in order to complete the reaction. The reaction is preferably performed under nitrogen blanket and preferably a vacuum such as 0.1 to 200 mm Hg; or most preferably about 60 mm Hg. As known in the art, progress of the reaction can be monitored by gas chromatography. In a preferred embodiment, the reactants are heated to a temperature of about 100° C. for a period of about 5 hours. In one embodiment, a solvent such as, but not limited to, toluene, methyl isobutyl ketone, or pentyl acetate is utilized. Preferably, a means is used to remove the water formed, such as a distillation or a Dean-Stark trap with a refluxing solvent, for example. As illustrated in the above mechanisms, the esterification reaction results in the thiocarbonate compound having at least one terminal hydrophobic group thereon.

The hydrophobe-terminated thiocarbonate compound is then polymerized as described hereinbelow with at least one unsaturated vinyl hydrophilic monomer, such as (meth)acrylic acid, or a mixture of monomers containing at least one hydrophilic monomer to give the amphiphilic associative thickener polymers.

In another embodiment, hydrophobic pendant group(s) are added to the thiocarbonate compound via a polymerization reaction of a hydrophobe group containing monomer with the thiocarbonate compound. The hydrophobe group containing unsaturated monomers are described hereinabove. Example reaction mechanisms are as follows:

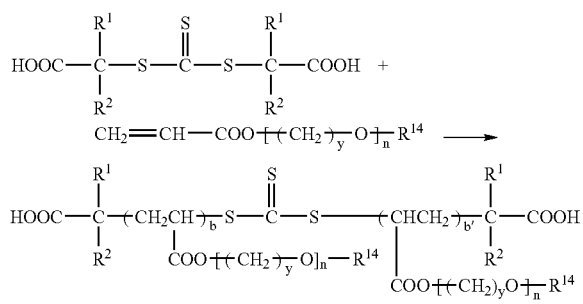

-continued

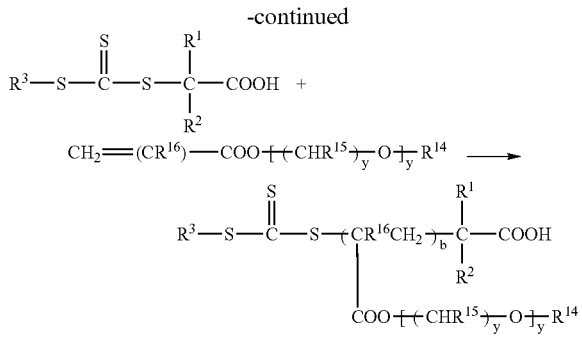

wherein b and b' are 1 to about 20, and preferably about 1 to about 5, and $R^1$, $R^2$, $R^3$, $R^{14}$, $R^{15}$, $R^{16}$, y, and n are defined herein. The polymerization reactions, conditions, etc. are described hereinbelow with respect to the polymerization of hydrophilic group containing monomers and is herein incorporated by reference. As evident from the combination of the above reaction mechanisms, in one embodiment at least one hydrophobic terminal group and at least one hydrophobic pendant group is incorporated into the thiocarbonate compound, preferably via the esterification and polymerization reactions as described.

Hydrophilic Groups

In addition to the at least one hydrophobe group containing monomer(s) present on the thiocarbonate compound, the associative thickeners include at least one hydrophilic group, preferably repeat units derived from one or more hydrophilic group containing unsaturated monomers. Generally, the hydrophilic group containing compounds are acrylic type monomers such as acrylic acid, methacrylic acid, (meth)acrylic acid salts, acrylamide, methacrylamide, dialkylaminoalkyl(meth)acrylate, alkyl or hydrogen halide salts of aminoalkyl(meth)acrylate, hydroxy alkyl(meth)acrylate, or combinations thereof. In one embodiment, the unsaturated acrylic-based monomers have the following general formulae: $CH_2=C(CH_3)-COOX$, $CH_2=CH-COOX$, or $CH_2=C(CH_3)-CONH_2$, or $CH_2=CHCONH_2$, wherein X is H; a metal ion such as Li, Na, K, or Ca; an amino group such as an alkylamino or dialkylamino group having from 1 to about 6 carbon atoms or an alkyl/hydrogen halide salt thereof; or hydroxy alkyl group having from 1 to 6 carbon atoms. Other hydrophilic monomers include unsaturated polymerizable acids such as maleic acid, fumaric acid, itaconic acid, crotonic acid, oleic acid, cinnamic acid or salts thereof; and unsaturated polymerizable monomers containing sulfonic acid or a salt thereof.

Specific hydrophilic monomers or comonomers for use in the present invention include, but are not limited to, the following: acrylic acid, methacrylic acid, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, 2-dimethylaminoethyl acrylate and its alkyl/hydrogen halide salts, 2-dimethylaminoethyl methacrylate and its alkyl/hydrogen halide salts, 2-hydroxyethyl acrylate, hydroxypropyl acrylate (all isomers), hydroxybutyl acrylate (all isomers), polyethylene glycol monoacrylate, polyethylene glycol monomethacrylate, polypropylene glycol monoacrylate, polypropylene glycol monomethacrylate, N,N-diethylaminoethyl acrylate, maleic acid, fumaric acid, itaconic acid, crotonic acid, oleic acid, cinnamic acid, styrene sulfonic acid, and 2-acrylamido-2-methylpropane sulfonic acid (AMPS). Some preferred monomers are acrylic acid, methacrylic acid, and 2-hydroxyethyl acrylate.

In a further embodiment other monomers, other than the hydrophobic or hydrophilic monomers described above, are optionally polymerized into the backbone of the thiocarbonate compound during a polymerization reaction. Examples of monomers include, but are not limited to, vinyl acetate; styrene; diene monomers having a total of from 4 to 12 carbon atoms with examples including, but not limited to, 1,3-butadiene, isoprene, 1,3-pentadiene, 2,3-dimethyl-1-3-butadiene, 2-methyl-1,3-pentadiene, 2,3-dimethyl-1,3-pentadiene, 2-phenyl-1,3-butadiene, and 4,5-diethyl-1,3-octadiene; α-methyl styrene; and $C_1$-$C_{12}$ alkyl styrenes with substitute groups either on the chain or on the ring or both.

In order to initiate the polymerization process, it is often desirable to utilize an initiator as a source for initiating free radicals. Generally, the source of initiating radicals can be any suitable method of generating free radicals such as the thermally induced homolytic scission of a suitable compound(s) (thermal initiators such as peroxides, peroxyesters, or azo compounds), the spontaneous generation from monomer, redox initiating systems, photochemical initiating systems or high energy radiation such as electron beam, X- or gamma-radiation. The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture. The thiocarbonate compounds of the invention can serve as an initiator, but the reaction must be run at a higher temperature.

Thermal initiators are chosen to have an appropriate half-life at the temperature of polymerization. The initiators can include one or more of the following compounds: 2,2'-azobis(isobutyronitrile)(AIBN), 2,2'-azobis(2-cyano-2-butane), dimethyl 2,2'-azobisdimethylisobutyrate, 4,4'-azobis(4-cyanopentanoic acid), 1,1'-azobis(cyclohexanecarbanitrile), 2-(t-butylazo)-2-cyanopropane, 2,2'-azobis[2-methyl-N-(1,1)-bis(hydoxymethyl)-2-hydroxyethyl] propionamide, 2,2'-azobis[2-methyl-N-hydroxyethyl)]-propionamide, 2,2'-azobis(N,N'-dimethyleneisobutyramidine)dihydrochloride, 2,2'-azobis (2-amidinopropane)dihydrochloride, 2,2'-azobis(N,N'-dimethyleneisobutyramine), 2,2'-azobis(2-methyl-N-[1,1-bis(hydroxymethyl)-2-hydroxyethyl]propionamide), 2,2'-azobis(2-methyl N-[1,1-bis(hydroxymethyl)ethyl] propionamide), 2,2'-azobis[2-methyl-N-(2-hydroxyethyl) propionamide], 2,2'-azobis(isobutyramide)dehydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butylperoxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroylperoxide, potassium peroxydisulfate, ammonium peroxydisulfate, di-t-butyl hyponitrite, and dicumyl hyponitrite.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems production under the conditions of the polymerization. These initiating systems can include, but are not limited to, combinations of the following oxidants, potassium peroxydisuffate, hydrogen peroxide, t-butyl hydroperoxide and reductants, iron (11), titanium (111), potassium thiosulfite, and potassium bisulfite.

Other suitable initiating systems are known to those of ordinary skill in the art, and are described in recent texts. See, for example, Moad and Solomon "The Chemistry of Free Radical Polymerization", Pergamon, London. 1995. pp 53-95.

The preferred initiators of the present invention are 2,2'-azobis(isobutyronitrile)(AlBN), or 4,4'-azobis(4-cyanopentanoic acid), or 2,2'-azobis(2-cyano-2-butane), or 1,1'-azobis (cyclohexanecarbanitrile). The amount of initiators utilized in the polymerization process can vary widely as generally from about 0.001 percent to about 99 percent, and desirably from about 0.01 percent to about 50 or 75 percent based on the total moles of thiocarbonate compound utilized. Preferably small amounts are utilized, such as from about 0.1 percent to about 5, 10, 15, 20, or 25 mole percent based on the total moles of thiocarbonate compound. In order to form polymers which are predominately telechelic, initiators other than the thiocarbonate compounds are utilized in lesser amounts, such as from about 0.001 percent to about 5 percent, desirably from about 0.01 percent to about 4.5 percent, and preferably from about 0.1 percent to about 3 percent based on the molar equivalent to the total moles of thiocarbonate compound utilized.

Optionally, as noted above, solvents may be utilized in the free radical polymerization process. Examples of such solvents include, but are not limited to, $C_6$-$C_{12}$ alkanes, toluene, chlorobenzene, acetone, t-butyl alcohol, and dimethylformamide. The solvents are chosen so that they do not chain transfer themselves. The amount of solvent when utilized in the present invention polymerization process is generally from about 10 percent to about 500 percent the weight of the monomer, and preferably from about 50 percent to about 200 percent the weight of the monomer utilized in the polymerization.

In order to form thiocarbonate compounds having monomer repeat units therein, a predetermined amount of thiocarbonate compound, optionally having hydrophobe groups already present thereon is added to a suitable reaction vessel along with a predetermined amount of monomer(s), optionally solvent, and optionally initiator. The amount of thiocarbonate compound utilized depends on the desired molecular weight of the polymer to be formed and can be calculated as known to one of ordinary skill in the art. A formula for calculating the amount of thiocarbonate compound (TC) is as follows:

$$\text{Mn of polymer} = \left(\frac{\text{Weight of monomer} \times \text{molecular weight } TC}{\text{Weight of } TC}\right) + \text{molecular weight of } TC$$

In one embodiment, if the thiocarbonate compound utilized in the polymerization reaction does not contain a hydrophobe group, at least one monomer containing such a hydrophobe group is utilized in order to produce a hydrophobe group containing thiocarbonate polymer or copolymer.

The resulting polymers or copolymers are either telechelic polymers with identical functional groups at the ends of the chain, or a polymer having a single functional end group and also an initiator terminated chain (formed by using a conventional initiator such as AlBN). As stated above, the ratios between the resulting polymers can be controlled to give desired results and generally depends on the amount of initiator utilized. Obviously, if the initiator is only a thiocarbonate compound of the present invention, the resulting polymers are always telechelic. The greater the amount of the other initiator utilized, proportionally decreases the amount of telechelic polymers formed. The number of repeat groups from all sources, i.e., hydrophobic or hydrophilic group containing monomers, or other monomers, or a combination thereof incorporated into each thiocarbonate compound is generally from about 1 to about 400, desirably from about 1 to about 200, and preferably from about 2 to about 80. Inasmuch as one or more hydrophilic group containing monomers and optionally one or more hydrophobic group containing monomers or other monomers which are generally neither hydrophilic or hydrophobic can be utilized, it is to be understood that repeat groups of the polymers or copolymers of the present invention can be the same or different, respectively. That is, random copolymers, terpolymers, etc., can be formed within either of the repeat groups noted, as well as block copolymers which can be formed by initially adding one monomer and then subsequently adding a different monomer (e.g., an internal block copolymer). In one embodiment, the number of monomers polymerized into the backbone of the thiocarbonate compound is chosen so that the associative thickener imparts a composition with a usable or practical low shear viscosity.

The reaction conditions are chosen so that the temperature utilized will generate a radical in a controlled fashion, wherein the temperature is generally from about room temperature to about 200° C. The reaction can be run at temperatures lower than room temperature, but it is impractical to do so. The temperature often depends on the initiator chosen for the reaction, for example, when AlBN is utilized, the temperature generally is from about 40° C. to about 80° C., when azodicyanodivaleric acid is utilized, the temperature generally is from about 50° C. to about 90° C., when di-t-butylperoxide is utilized, the temperature generally is from about 110° C. to about 160° C., when a thiocarbonate is utilized, the temperature is generally from about 80° C. to about 200° C.

The polymerization process of this invention can be carried out in emulsion, solution or suspension, in either a batch, semi-batch, continuous, or feed mode. In the case of emulsion or suspension polymerization, the medium will often be predominately water and conventional stabilizers, dispersants and other additives can be present. For solution polymerization, the reaction medium can be chosen from a wide range of media to suit the monomer(s) being used.

Examples of polymerization mechanisms incorporating hydrophilic monomers into thiocarbonate compounds having a terminal hydrophobe group already present thereon are as follows:

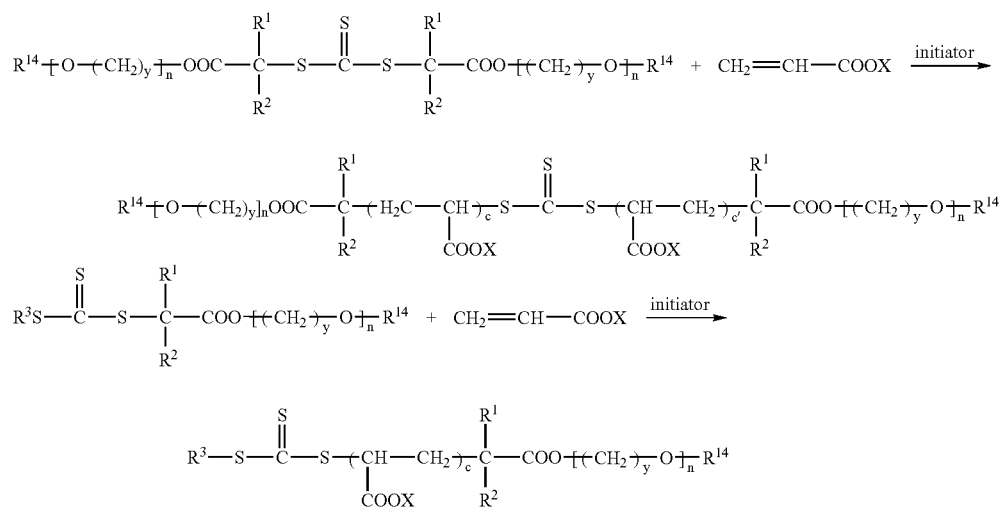

wherein c and c' are each 1 to about 200, and $R^1$, $R^2$, $R^3$, $R^{14}$, n and y are defined herein.

Example reaction mechanisms, adding monomers having a hydrophobic group, as well as hydrophilic monomers to a thiocarbonate compound are as follows:

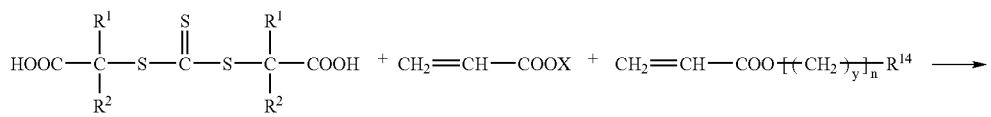

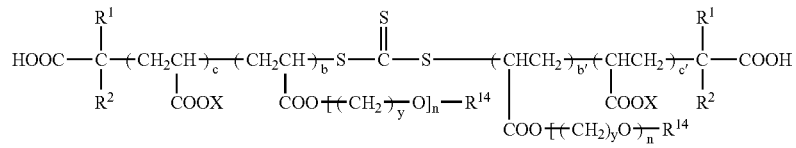

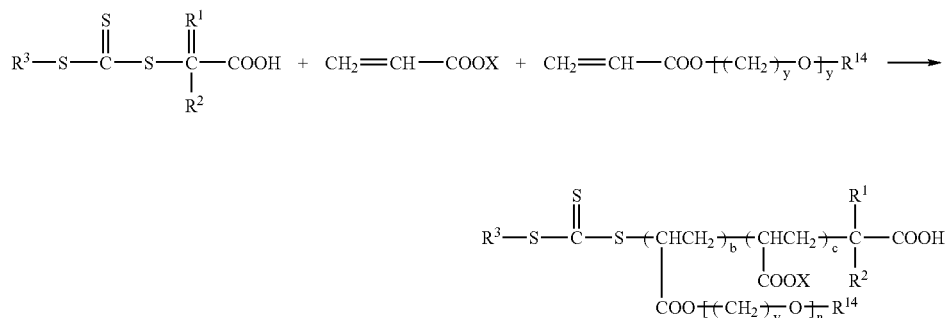

wherein b, b', c, c', n, $R^1$, $R^2$, $R^3$, $R^{14}$ and y are defined herein.

Once the polymerization reaction has been carried out to a desired degree, the thiocarbonate polymers or copolymers can be neutralized in any suitable base such as, but not limited to, ammonium hydroxide, sodium hydroxide, and potassium hydroxide. The polymer is preferably subsequently isolated by methods known to those of ordinary skill in the art before being utilized as an associative thickener. If the polymerization solvent is water, or water-soluble, then the aqueous solution of the neutralized polymer can be used directly.

The associative thickeners of the present invention are preferably utilized in aqueous compositions or systems intended for various purposes, but are particularly preferred for use in aqueous latex paints and coatings in order to modify viscosity and thereby improve the rheology of the system. Additional aqueous systems in which the associative thickeners are useful include, but are not limited to, aqueous coating compositions for the paper, leather and textile industries, well flooding compositions and drilling muds, detergents, adhesives, waxes, polishes, cosmetics, toiletries, topical pharmaceuticals, pesticidal compositions, and agricultural compositions. The thiocarbonate associative thickeners may be used for thickening water alone, with the resulting solution then being utilized in a second system to be thickened.

In the textile field, the associative thickeners are useful in textile finishes, bonding agents for wovens and non-wovens, tie coats, and dyeing and coloring compositions. The aqueous compositions may be simple aqueous dispersions or even oil in water emulsions. Cosmetic compositions include, but are not limited to, hand creams, hand lotions, cleansing creams, hair sprays, hair creams, cold waving lotions, shampoos, cream rinses and the like.

The thiocarbonate thickeners of this invention can be effectively utilized in consumer paints and industrial coatings. Paints and industrial coatings typically comprise an organic polymeric binder, pigments, fillers, and various additives to provide sufficiently fluid compositions to flow out and form a continuous film adapted to be dried or cured to form a hard protective film on a substrate. Pigments can be organic or inorganic and functionally contribute to opacity and color in addition to durability and hardness of the dried paint film.

Consumer paints are ambient air drying aqueous based latex compositions applied to architectural interior and/or exterior surfaces for aesthetic appearance and protection of the substrate. Latex paints ordinarily are thickened to promote suspension of the pigment in the latex polymer and provide proper rheology to enable application and flow without sagging. Other additives such as coalescing solvent, gloss control agents, and stabilizing agents can be added as desired.

Latex polymers are aqueous copolymerized ethylenically unsaturated monomers comprising primarily vinyl and/or acrylic monomers. Acrylic monomers include lower alkyl esters of acrylic or methacrylic acid having a lower alkyl chain containing form 1 to about 12 or more carbon atoms. Useful acrylic monomers include for example acrylate and methacrylate esters of methyl, ethyl, propyl, butyl, 2-ethyl hexyl, decyl and iso decyl, benzyl, and similar acrylates and methacrylates, as well as hydroxyethyl and hydroxypropyl acrylates and methacrylates, acrylic acids including acrylic, methacrylic and similar lower alkyl acrylic acids. Useful vinyl monomers include vinyl esters such as vinyl acetate, vinyl propionate, vinyl butyrates, vinyl benzoates and similar vinyl esters, vinyl halides, vinyl aromatic hydrocarbons such as styrene and low alkyl substituted styrenes, chlorostyrene, vinyl toluene and divinyl benzene, and vinyl aliphatic hydrocarbons such as olefins and conjugated dienes. Other useful ethylenically unsaturated monomers include allylic monomers and amido monomers such as acrylamide and methacrylamide and can be added as desired. Latex polymers can be produced by copolymerizing ethylenically unsaturated monomers in an aqueous polymerization medium by adding the monomers to water over a period of time along with surfactants and polymerizing free radical initiators such as peroxides or persulfates.

Industrial thermosetting coatings can be coreactive aqueous emulsion latex polymers or thermosetting water dispersed polymers. Water dispersed polymers ordinarily comprise preformed carboxyl functional polymers prepared in organic solvents and subsequently dispersed into water using a fugitive base such a primary, secondary, or tertiary amine. Useful polymers include for instance polyester, polyacrylates, polyepoxides, polyamides, polyamines, and polyurethanes. Water dispersed thermosetting polymers can be thermoset by heating with a crosslinking agent such as an aminoplast resin.

The thiocarbonate associative thickeners of the present invention may be added to any aqueous composition in an effective amount to provide an adequate or desired level of thickening to the composition. Typically, the active weight of thiocarbonate associative thickener utilized ranges generally from about 0.01 to about 2 or about 5 parts, desirably from about 0.05 to about 1.5 parts, and preferably from about 0.1 to about 1 part by weight based on 100 parts by weight of a composition. In one embodiment, a composition comprises water and a latex polymer. As known in the art, aqueous compositions can include any desired combination of additives or other adjuvants, with examples including, but not limited to, pigments such as titanium dioxide and carbon black; a defoamer; a solvent; a neutralizer; a dispersant; a biocide; a plasticizer, or a stabilizer. It is to be understood that the amount of the associative thickeners may be higher or lower depending on the particular system utilized, other additives present and other variables understood or known to those of ordinary skill in the art.

The present invention will be better understood by reference to the following examples which serve to describe, but not to limit, the present invention.

Synthesis of Hydrophobe Group Containing Trithiocarbonate Compounds

EXAMPLE 1

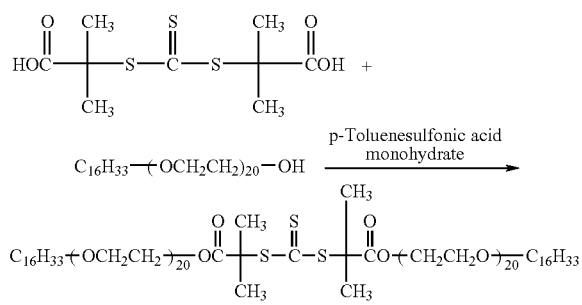

5.78 grams trithiocarbonate, 50 grams Brij® 58 a hydrophobe group containing compound from Uniqema, and 0.5 gram p-toluene sulfonic acid were mixed in a 100 ml round bottom flask with a stirrer and heated to about 130° C. under 60 mmHg vacuum to distill off 0.15 ml water in 30 minutes using a condenser and a receiver. 0.5 g more of the acid was added and the distillation was continued at about 130° C. for 5 more hours to produce the product shown above. The contents of the flask were poured into a reaction vessel and used directly in the polymerization described in Example 2.

EXAMPLE 1B

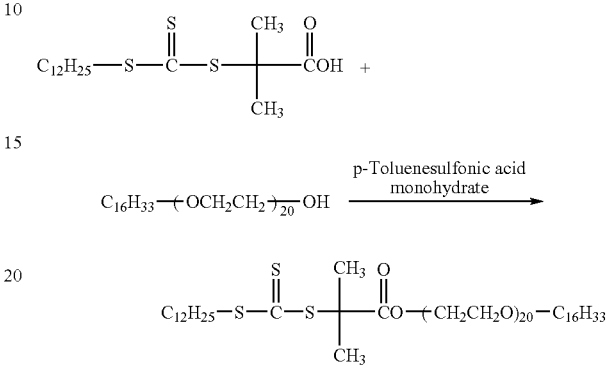

In a 100 ml reaction vessel equipped with a magnetic stirrer, mantle, thermowatch, short-column condenser, cow receiver, and thermometers, 117.97 grams of hydrophobe group containing compound (Brij® 58) and 1.90 grams of p-toluenesulfonic acid monohydrate were added. The reactants were heated to about 80° C. and subsequently 36.4 grams of the trithiocarbonate compound was added. A partial vacuum to 60 mmHg mercury was applied and the temperature was increased to about 110° C. for a period of five hours to collect water that was formed and produce the product shown above. The product can be used "as is" as in Example 2B, or can be placed into toluene and washed with an aqueous base such as a 10% sodium hydroxide or sodium carbonate solution to remove residual acid catalyst, and then concentrated.

Polymerization of Hydrophilic Group Containing Repeat Units into Trithiocarbonate Hydrophobe Group Containing Compounds to Form Associative Thickeners

EXAMPLE 2

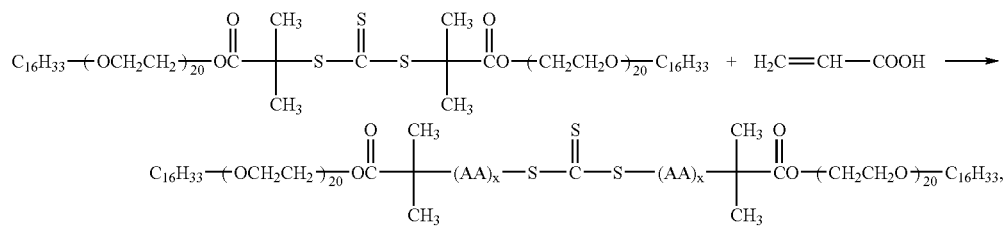

wherein Mn is about 10,000

59.28 grams crude product from Example 1, and 200 grams acrylic acid were polymerized in a 1 liter round bottom flask with 0.3 gram AIBN and 200 grams t-butyl alcohol at about 80° C. for about 5 hours under nitrogen atmosphere. T-butyl alcohol was removed in a rotary evaporator. 600 ml water was added and the solution was neutralized with 50% NaOH (160 g) to a pH of about 8 to about 9. The viscous aqueous solution was used in the associative thickener evaluation hereinbelow.

EXAMPLE 2B

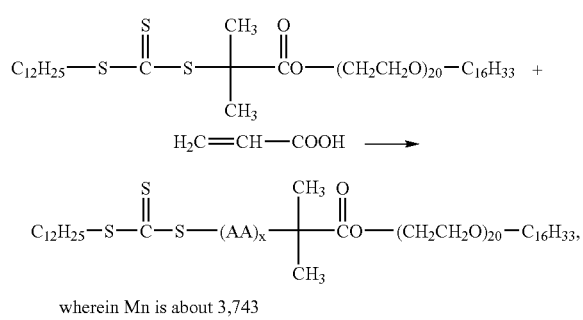

wherein Mn is about 3,743

In a 500 ml, 3 port reaction vessel equipped with mechanical stirrer, nitrogen blanket, oilbath, j-chem thermocouple unit, and a condenser, 4.9 grams of the hydrophobe group containing trithiocarbonate compound of Example 1B, 45.1 grams acrylic acid, 200 grams of water, and 0.0271 grams 2,2'-azobis(2-methylproprionamidine)dihydrochloride were added. The reactants were heated to about 65° C. until an exotherm reaction took place. Afterwards, the reactants were heated to about 80° C. for a period of about 3 hours. An aqueous NaOH solution was added to adjust the pH to about 8 and the solid content to about 20%.

EXAMPLE 3

Synthesis of Hydrophobe Group Containing Dithiocarbonate Compounds

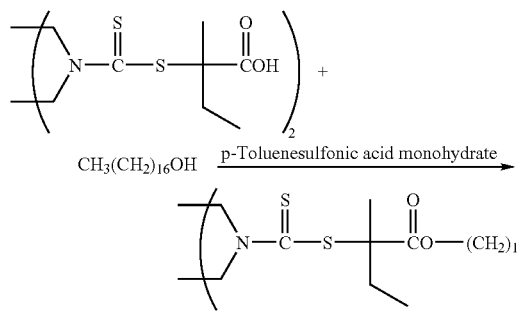

In a 100 ml, 3 port reaction vessel equipped with a mechanical stirrer, mantle, thermowatch, short-column condenser, cow receiver, thermometers, and a nitrogen blanket, 27.68 grams of hydrophobe group containing compound and 4.34 grams of p-toluenesulfonic acid monohydrate were added. The reactants were heated to about 80° C. and 25 grams of the trithiocarbonate compound was added. A partial vacuum to 60 mmHg mercury was applied and the temperature was increased to about 110° C. for a period of five hours to produce the product shown above.

EXAMPLE 4

Polymerization of Acrylic Acid Repeat Units into Hydrophobe Group Containing Dithiocarbonate Compound from Example 3

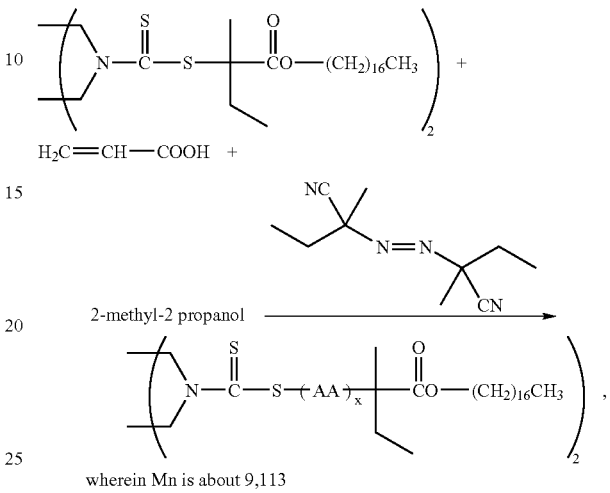

wherein Mn is about 9,113

In a 150 ml, 3 port reaction vessel equipped with a mechanical stirrer, nitrogen blanket, oilbath, j-chem thermocouple unit, and a condenser, 1.33 grams of the hydrophobe group containing dithiocarbonate compound, 13.67 grams acrylic acid, 15 grams of 2-methyl-2-propanol, and 0.0086 grams Vazo® 67 were added. The reactants were heated to about 65° C. until an exotherm reaction took place. Afterwards, the reactants were heated to about 80° C. for a period of about 7 hours to produce the product shown above.

EXAMPLE 5

Synthesis of Hydrophobe Group Containing Dithiocarbonate Compounds

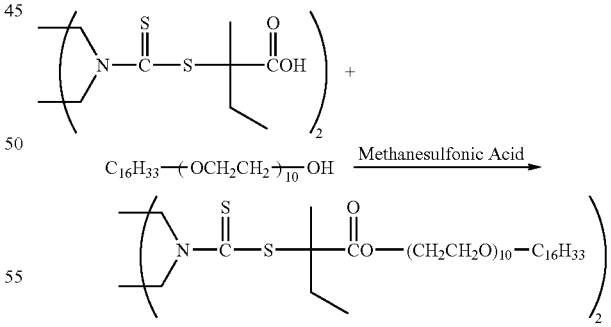

In a 50 ml, 3 port reaction vessel equipped with a mechanical stirrer, mantle, thermowatch, short-column condenser, cow receiver, and thermometers, 6.57 grams of dithiocarbonate, 21.51 grams of hydrophobe Brij® 56, and 0.5 grams of methanesulfonic acid were added. The reactants were heated to about 110° C. until an exotherm reaction took place. A partial vacuum to 60 mmHg mercury was applied and the temperature was increased to about 130° C. for a period of about 5.5 hours to produce the product shown above.

EXAMPLE 6

Polymerization of Acrylic Acid Repeat Units into Hydrophobe Group Containing Dithiocarbonate Compound from Example 5

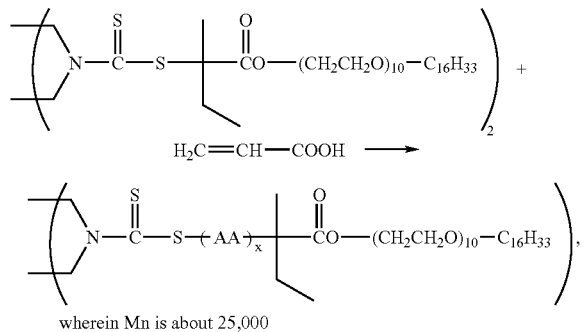

wherein Mn is about 25,000

In a 250 ml, 3 port reaction vessel equipped with mechanical stirrer, nitrogen blanket, oilbath, j-chem thermocouple unit, and a condenser, 1.67 grams of the hydrophobe group containing dithiocarbonate compound, 20 grams acrylic acid, 86.68 grams of water, and 0.013 grams 2,2'-azobis(2-methylproprionamidine)dihydrochloride were added. The reactants were heated to about 65° C. until an exotherm reaction took place. Afterwards, the reactants were heated to a controlled temperature of about 66° C. for a period of about 5.5 hours to produce the product shown above.

EXAMPLE 7

Polymerization of Acrylic Acid Repeat Units into Hydrophobe Group Containing Dithiocarbonate Compound from Example 5

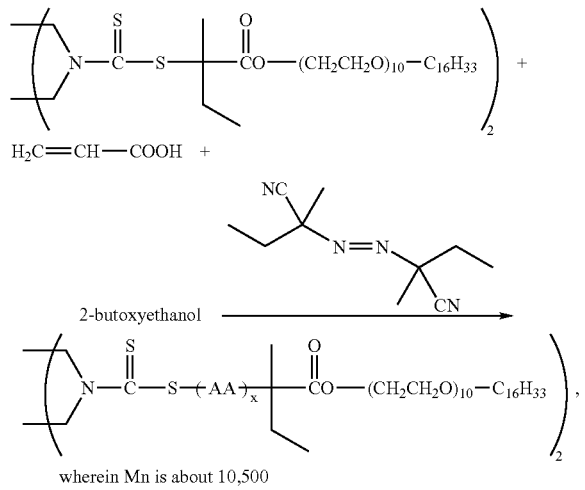

wherein Mn is about 10,500

In a 150 ml, 3 port reaction vessel equipped with a mechanical stirrer, nitrogen blanket, oilbath, j-chem thermocouple unit, and a condenser, 4.21 grams of the hydrophobe group containing dithiocarbonate compound, 20.79 grams acrylic acid, 25 grams of 2-butoxyethanol, and 0.01 grams Vazo® 67 (catalyst shown above) were added. The reactants were heated to about 65° C. until an exotherm reaction took place. Afterwards, the reactants were heated to about 82° C. for a period of about 6 hours to produce the product shown above.

EXAMPLE 8

Polymerization of Acrylic Acid Repeat Units into Hydrophobe Group Containing Dithiocarbonate Compound from Example 5

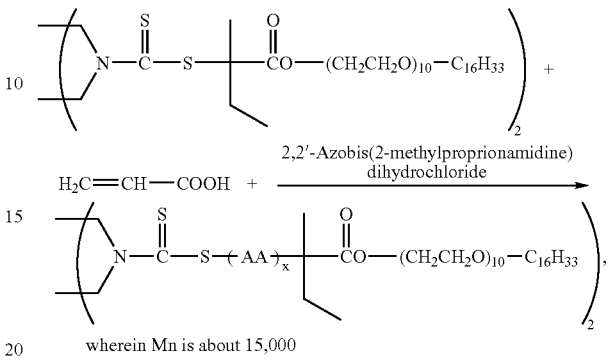

wherein Mn is about 15,000

In a 250 ml, 3 port reaction vessel equipped with mechanical stirrer, nitrogen blanket, oil bath, j-chem thermocouple unit, and a condenser, 2.93 grams of the hydrophobe group containing trithiocarbonate compound, 20 grams acrylic acid, 91.71 grams of water, and 0.013 grams 2,2'-azobis(2-methylproprionamidine)dihydrochloride were added. The reactants were heated to about 65° C. for about 5 hours to produce the product shown above.

Confirmation of Viscosity Enhancing Properties

In order to illustrate the viscosity enhancing properties of the associative thickeners of the present invention, the Example 2B associative thickener trithiocarbonate polymer containing acrylic acid repeat units and hydrophobic terminal groups was added in various amounts to the aqueous latex paint composition (244.565 g) listed in Table 3. The thickening ability of the compound is documented in Table I set forth hereinbelow.

TABLE 1

| ASSOCIATIVE THICKENER | | | | |
|---|---|---|---|---|
| Active parts per 100 parts of aqueous composition | active weight | grams | ICI Value (poise) | KU Value (Krebs unit) |
| 0.37 | 20% | 4.5 | 0.4 | 65.7 |
| 0.68 | 20% | 8.3 | 0.7 | 95.2 |
| 0.89 | 20% | 10.9 | 1.6 | 110.0 |

As shown in the above table, when the amount of the associative thickener is increased, both the ICI, high shear viscosity, and KU, low shear viscosity, values increase which indicate viscosity increases due to the associative thickening properties of the polymer.

Table 2 illustrates comparison of various associative thickeners of the present invention with prior art control thickeners, with Control 1 being a commercial hydrophobically-modified ethoxylated urethanes (HEURs) associative thickener and Control 2 being a commercial hydrophobically-modified alkali-swellable emulsions (HASE) polyacrylate associative thickener. Table 2 sets forth the amount of the active thickener present in an associative thickener composition which is added to the aqueous latex paint formulation set forth in Table 3. As illustrated in Table 2, the associative thickeners of the present invention produced excellent high shear viscosity and low shear viscosity value comparable or better than the prior art controls.

TABLE 2

Comparison of Associative Thickeners

| ASSOCIATIVE THICKENER | | | | | |
|---|---|---|---|---|---|
| | Active parts per 100 parts of aqueous composition | active weight | grams | ICI Value (poise) | KU Value (Krebs unit) |
| Example 2 | 1.08 | 10% | 26.6 | 1.0 | 68.4 |
| Example 4 | 1.08 | 10% | 26.6 | 1.9 | 105.8 |
| Example 6 | 0.61 | 10% | 15 | 1.2 | 128.5 |
| Example 7 | 0.57 | 10% | 14 | 1.2 | 108.6 |
| Example 8 | 0.61 | 10% | 15 | 1.3 | 138.2 |
| Control 1- Aquaaflow NHS[a] 300 (HEUR) | 0.37 | 20% | 4.5 | 2.0 | 102.5 |
| Control 2- (HASE) | 0.38 | 30% | 3.1 | 0.7 | >145 |

[a] Hercules Corp.

Table 3 represents a standard aqueous latex paint formulation utilized in the industry to produce a high gloss paint. In the noted examples above, the associative thickeners were added to this composition in various amounts to illustrate the thickening abilities and effects on viscosity by the compounds of the present invention.

TABLE 3

Base Paint Cormposition Used in Examples

| Ethylene Glycol | 8.875 |
|---|---|
| TiO$_2$ Pigment (Kronos 4311) | 79.05 |
| Water | 1.59 |
| Defoamer (Foamstar A34) | 0.25 |
| Solvent (DB) | 1.9 |
| Neutralizer (AMP 95) | 0.6 |
| Dispersant (BYK 333) | 0.075 |
| Premix top 7 | |
| Add | |
| Styrene acrylate latex (Carboset 7705) | 143.40 |
| Defoamer (Foamstar A34) | 0.725 |
| Water | 2.4 |

TABLE 3-continued

Base Paint Cormposition Used in Examples

| Mix 5 minutes | |
|---|---|
| Add | |
| Solvent (alcohol) (Texanol) | 0.95 |
| Mix 5 minutes | |
| Biocide (Proxcel GXL) | 0.25 |
| Biocide (Troy P20T) | 0.825 |
| Defoamer (BYK 024) | 0.475 |
| Dispersant(Tamol 165A) | 0.475 |
| Plasticizer (Carbowax 200) | 2.25 |
| Defoamer (BYK 024) (REPEAT?) | 0.475 |
| Associative Thickener | Varied |
| Total | 244.565 + associative thickener weight |
| Premix top 6 | Add and mix for 5 minutes |

Table 4 illustrates the increase in viscosity of the aqueous latex paint composition of Table 3 when an increasing amount of different associative thickeners are utilized therein. The results illustrate that the associative thickeners of the present invention can be used to effectively modify the viscosity of various compositions.

TABLE 4

EFFECT OF VARYING AMOUNTS OF ASSOCIATIVE THICKENER ON VISCOSITY

| | ASSOCIATIVE THICKENER | | | | |
|---|---|---|---|---|---|
| | Active parts per 100 parts of aqueous paint composition | Percent active thickener | Grams total thickener composition | ICI Value (poise) | KU Value (Krebs unit) |
| Example 8 | 0.41 | 10% | 10 | 0.9 | 116.4 |
| Example 8 | 0.61 | 10% | 15 | 1.3 | 138.2 |
| Example 8 | 0.82 | 10% | 20 | 1.5 | Too thick |
| Example 6 | 0.41 | 10% | 10 | 0.9 | 108.5 |
| Example 6 | 0.61 | 10% | 15 | 1.2 | 128.5 |
| Example 6 | 0.82 | 10% | 20 | 1.5 | Too thick |

In accordance with the patent statutes, the best mode and preferred embodiment have been set forth, the scope of the invention is not limited thereto, but rather by the scope of the attached claims.

What is claimed is:

1. A thiocarbonate composition comprising a reaction product of: a) at least one hydrophobe group compound; and optionally b) at least one hydrophilic group compound; and c) a thiocarbonate compound having the formula:

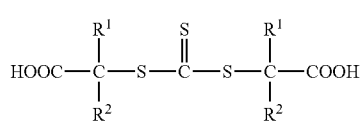

(i)

wherein $R^1$ and $R^2$, independently, are selected from a linear or branched alkyl having from 1 to 6 carbon atoms, a substituted alkyl having from 1 to 6 carbon atoms, substituted and unsubstituted aryl, $R^1$ and $R^2$ can form a substituted or unsubstituted cyclic ring having from 5 to 12 total carbon atoms; wherein said substituents, independently, are selected from an alkyl having from 1 to 6 carbon atoms, aryl, a halogen which can be the same or different, cyano, an ether having a total of from 2 to 20 carbon atoms, and a nitro group; or

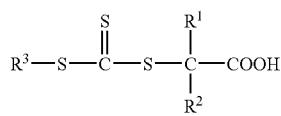

(ii)

wherein $R^3$ is selected from benzyl, a $C_1$ through $C_{18}$ alkyl, a substituted $C_1$ to $C_{18}$ alkyl, wherein said substituted group is selected from halogen, hydroxyl, alkoxy, a $C_1$ to $C_{18}$ hydroxyalkyl, aralkyl, cyanoalkyl, aminoalkyl, carboxyalkyl, carboalkoxyalkyl, and mercaptoalkyl, and wherein $R^1$ and $R^2$, independently, are as set forth above; or

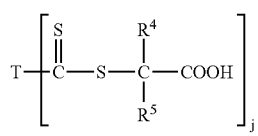

(iii)

wherein j is 1 or 2, with the proviso that when j is 1, T is (—$NR^6R^7$), when j is 2, T is a divalent radical having a nitrogen atom directly connected to each carbon atom of the two thiocarbonyl groups; wherein $R^4$ and $R^5$, independently, are the same or different, are optionally substituted as defined for $R^1$ and $R^2$, and are selected from a linear or branched alkyl having from 1 to 12 carbon atoms, aryl having from 6 to 18 carbon atoms, $R^4$ and $R^5$ can form a substituted or unsubstituted cyclic ring having from 3 to 12 carbon atoms, wherein said substituents, independently, are selected from an alkyl having from 1 to 6 carbon atoms, aryl, halogen, cyano, an ether having a total of from 2 to 20 carbon atoms, a nitro group, and combinations thereof; wherein $R^6$ and $R^7$, independently, are the same or different, optionally substituted as defined for $R^1$ and $R^2$, and are selected from hydrogen, a linear or branched alkyl having from 1 to 18 carbon atoms, aryl, aryl alkyl having from 6 to 18 carbon atoms, optionally saturated or unsaturated, arylalkyl having from 7 to 18 carbons, alkenealkyl having from 3 to 18 carbon atoms, polyalkylene glycol ether having from 3 to 200 carbon atoms, and amine, or $R^6$ and $R^7$ can form a cyclic ring with the nitrogen atom having a total of 4 to 12 carbon atoms; or

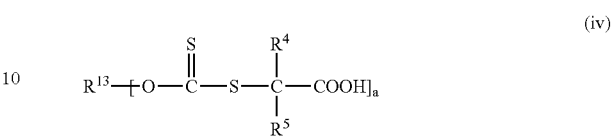

(iv)

wherein $R^4$ and $R^5$ are as defined above; wherein $R^{13}$ is optionally substituted, and is selected
from linear or branched alkyl having from 1 to 12 carbon atoms, aryl optionally saturated or unsaturated, arylalkyl having from 7 to 18 carbon atoms, acyl, alkene, alkenealkyl having from 3 to 18 carbon atoms, an alkylene group, an alkoxyalkyl, polyalkylene glycol, polyalkylene glycol monoalkyl ether having from 3 to 200 carbon atoms, and 2-trifluoroethyl; wherein when $R^{13}$ is optionally substituted the substituent is selected from alkyl having from 1 to 6 carbon atoms, aryl, halogen, a cyano group, an amino group, an alkene group, an alkoxycarbonyl group, an aryloxycarbonyl group, a carboxy group, an acyloxy group, a carbamoyl group, an alkylcarbonyl group, an alkylarylcarbonyl group, an arylcarbonyl group, an arylalkylcarbonyl group, a phthalimido group, a maleimido group, a succinimido group, amidino group, guanidimo group, allyl group, epoxy group, alkoxy group, an alkali metal salt, a cationic substituent, a hydroxyl group, an ether having a total of from 2 to 20 carbon atoms, nitro, sulfur, phosphorous, a carboalkoxy group, and combinations thereof; and wherein "a" is 1 to 4; wherein said at least one hydrophobe group compound is represented by the formulae:

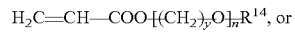

wherein $R^{14}$ is an alkyl group having from 3 to 50 carbon atoms; wherein each $R^{15}$, independently, is selected from hydrogen and an alkyl group of from 1 to 2 carbon atoms; wherein $R^{16}$ is hydrogen or a methyl group; wherein y is from 1 to 12; and wherein each n is the same or different and is 1 to 200; and wherein said at least one optional hydrophilic compound is selected from acrylic monomers, unsaturated polymerizable acids selected from maleic acid, fumaric acid, itaconic acid, crotonic acid, oleic acid, cinnamic acid, styrene sulfonic acid, and 2-acrylamido-2-methylpropane sulfonic acid, and salts thereof.

2. The composition according to claim 1, wherein said hydrophilic compound is selected from acrylic acid, methacrylic acid, a (meth)acrylic acid salt, acrylamide, methacrylamide, a dialkylaminoalkyl acrylate with each alkyl, independently, having from 1 to 6 carbon atoms, a dialkylaminoalkyl methacrylate with each alkyl, independently, having from 1 to 6 carbon atoms, a hydroxyalkyl acrylate with the alkyl having from 1 to 6 carbon atoms, a hydroxyalkyl methacrylate with the alkyl having from 1 to 6 carbon atoms, maleic acid, itaconic acid, crotonic acid, oleic acid, cinnamic acid or salt thereof, styrene sulfonic acid or salt, 2-acrylamido-2-methylpropane sulfonic acid or salt, and combinations thereof.

3. The composition according to claim 2, wherein $R^1$ and $R^2$ are independently, alkyl, substituted alkyl having one or more substituents, aryl, substituted aryl having from 1 to 6 substituents on the aryl ring; wherein j is 1; wherein $R^4$ and $R^5$, independently, are a phenyl group, an alkyl group having 1 to 10 carbon atoms, or wherein $R^4$ and $R^5$ are part of said cyclic ring; wherein $R^6$ and $R^7$, independently, are selected from phenyl, an alkyl group having from 1 to 10 carbon atoms, and hexamethylene; wherein $R^6$ and $R^7$ are part of said cyclic ring, or wherein j is 2 and T is:

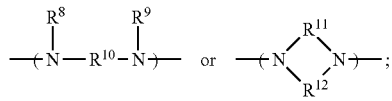

wherein $R^8$ and $R^9$, independently, are the same or different, are optionally substituted, and are selected from hydrogen, linear or branched alkyl having from 1 to 18 carbon atoms, aryl having from 6 to 18 carbon atoms, arylalkyl having from 7 to 18 carbon atoms, and alkenealkyl having from 3 to 18 carbon atoms; wherein $R^{10}$ is optionally substituted, or is non-existent, and is selected from an alkylene group having from 1 to 18 carbon atoms, a polyalkylene glycol either having from 3 to 200 carbon atoms; wherein said substituents, independently are selected from an alkyl having from 1 to 6 carbon atoms, aryl, halogen, cyano, an ether having a total of from 2 to 20 carbon atoms, a nitro group, and combinations thereof; and wherein $R^{11}$ and $R^{12}$, independently, are the same or different, and are optionally substituted, and are selected from an alkylene group having from 1 to 4 carbon atoms, or T is represented by the formula:

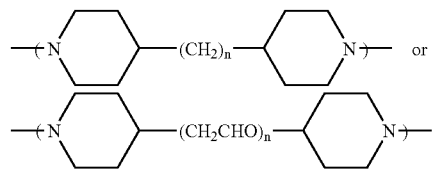

wherein n is 0 or 1 to 18.

4. The composition according to claim 3, wherein $R^1$ and $R^2$ are independently selected from methyl and phenyl; wherein $R^6$ and $R^7$, independently, are selected from phenyl, an alkyl group having from 1 to 10 carbon atoms, and hexamethylene; wherein $R^6$ and $R^7$ are part of said cyclic ring; and wherein "a" is 1 or 2.

5. The composition according to claim 3, wherein $R^{14}$ is an alkyl having from 6 to 30 carbon atoms; wherein y is 2 to 6; and wherein n is 1 to 50.

6. The composition according to claim 4, wherein $R^{14}$ is an alkyl having from 6 to 30 carbon atoms; wherein y is 2 to about 6; and wherein n is 1 to about 50.

7. The composition according to claim 1, wherein $R^{14}$ is an alkyl group having from 12 to 22 carbon atoms.

8. The composition of claim 1, wherein a residue of said at least one hydrophobe compound is located at the terminal end of said reaction product.

9. The composition of claim 8, wherein a residue of said at least one hydrophobe compound is pendant from said reaction product.

* * * * *